US008822377B2

(12) United States Patent
Zagar et al.

(10) Patent No.: US 8,822,377 B2
(45) Date of Patent: Sep. 2, 2014

(54) HERBICIDAL COMPOSITIONS COMPRISING TOPRAMEZONE AND PINOXADEN

(75) Inventors: Cyrill Zagar, Raleigh, NC (US); Andree van der Kloet, Heidelberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/984,407

(22) PCT Filed: Feb. 10, 2012

(86) PCT No.: PCT/EP2012/052248
§ 371 (c)(1),
(2), (4) Date: Aug. 8, 2013

(87) PCT Pub. No.: WO2012/107539
PCT Pub. Date: Aug. 16, 2012

(65) Prior Publication Data
US 2013/0310257 A1 Nov. 21, 2013

Related U.S. Application Data

(60) Provisional application No. 61/441,664, filed on Feb. 11, 2011.

(51) Int. Cl.
*A01N 25/26* (2006.01)
*A01N 43/36* (2006.01)
*A01N 43/00* (2006.01)

(52) U.S. Cl.
USPC .............................. 504/100; 504/138; 504/139

(58) Field of Classification Search
None
See application file for complete search history.

(56) References Cited

U.S. PATENT DOCUMENTS

| 6,534,444 B1 | 3/2003 | Sievernich et al. |
| 2003/0032559 A1 | 2/2003 | Ziemer et al. |
| 2004/0087445 A1 | 5/2004 | Ziemer et al. |
| 2007/0066481 A1 | 3/2007 | Ziemer et al. |
| 2010/0311588 A1 | 12/2010 | Gatzweiler et al. |

FOREIGN PATENT DOCUMENTS

| DE | 101 27 328 | * 12/2002 |
| DE | 102 37 461 | * 2/2004 |
| WO | WO 99/65314 | 12/1999 |
| WO | WO 9965314 | * 12/1999 |
| WO | WO 2004/080172 | 9/2004 |
| WO | WO 2004080172 | * 9/2004 |
| WO | WO 2007/073933 | 7/2007 |
| WO | WO 2008/049618 | 5/2008 |
| WO | WO 2010/136146 | 12/2010 |
| WO | WO 2010136146 | * 12/2010 |
| WO | 2011/067184 | 6/2011 |

OTHER PUBLICATIONS

Zollinger et al (Comparing Mesotrione, Tembotrione, and Topramezone, 2006 North Central Weed Science Society Proceedings, pp. 1-1—D2).*
International Search Report dated Apr. 23, 2012, prepared in International Application No. PCT/EP2012/052248.
International Preliminary Report on Patentability dated Dec. 10, 2012, prepared in International Application No. PCT/EP2012/052248.
Tomlin, CDS., "Pesticide Manual", 14$^{th}$ ed., 2006, BCPC Alton, Hampshire, UK, p. 843-844.
Tomlin, CDS., "Pesticide Manual", 14$^{th}$ ed., 2006, BCPC Alton, Hampshire, UK, p. 1047.
Zollinger, Richard, "Comparing mesotrione, tembotrione, and topramezone", 2006 North Central Weed Science Scociety Proceedings, Dec. 1, 2006, p. 1-1 XP550236339.

* cited by examiner

*Primary Examiner* — Alton Pryor
(74) *Attorney, Agent, or Firm* — Brinks Gilson & Lione

(57) ABSTRACT

The present invention relates to herbicidal compositions comprising topramezone and pinoxaden and optionally a herbicide safener compound such as cloquintocet. The present invention also relates to the use of these compositions for controlling undesirable vegetation, in particular in crops.

20 Claims, No Drawings

HERBICIDAL COMPOSITIONS COMPRISING TOPRAMEZONE AND PINOXADEN

This application is a National Stage application of International Application No. PCT/EP2012/052248, filed Feb. 10, 2012, which claims the benefit of U.S. Provisional Application No. 61/441,664, filed Feb. 11, 2011, the entire contents of which are hereby incorporated herein by reference.

The present invention relates to herbicidal compositions comprising topramezone and at least one further herbicidal compound and optionally a herbicide safener compound. The present invention also relates to the use of these compositions for controlling undesirable vegetation, in particular in crops.

BACKGROUND OF THE INVENTION

In crop protection, it is principally desirable in principle to increase the specificity and the reliability of the action of active compounds. In particular, it is desirable for the crop protection product to control the harmful plants effectively and, at the same time, to be tolerated by the useful plants in question.

Topramezone (IUPAC: [3-(4,5-dihydro-1,2-oxazol-3-yl)-4-mesyl-o-tolyl](5-hydroxy-1-methylpyrazol-4-yl)methanone), as well as its salts, esters, carbonates or thiocarbonates, is a well known herbicide active compounds (see C. D. S Tomlin (Ed.), The Pesticide Manual, 14th ed., 2006, BCPC Alton, Hampshire, UK, p. 1047). Topramezone is known to be an inhibitor of 4-hydroxyphenylpyruvatdioxygenase (4-HPPD inhibitor) and provides highly effective control of annual warm season grasses such as *Echinochloa-*, *Setaria-*, *Digitaria-* and *Panicum-*species, and of dicotyledonous weeds, like *Chenopodium-*, *Atriplex-*, *Amaranthus-*, *Solanum-*, *Galinsoga-*, *Stellaria media*, *Lamium-*, and *Veronica-*species (see e.g. A. Schönhammer et al. Zeitschrift für Pflanzenkrankheiten and Pflanzenschutz). The herbicidal activity and the activity spectrum, however are sometimes limited. In order to achieve a reliable herbicidal action, it has been recommended to apply topramezone in combination with adjuvants such as Dash®. Formulations of topramezone are marketed by BASF SE under the tradenames Clio® and Clio® super (co-formulation of topramezone with dimethenamid-P).

WO 99/65314 teaches that co-application of certain 4-benzoyl substituted 5-hydroxypyrazole compounds including topramezone with certain other herbicides may lead to a synergistic herbicidal activity.

WO 2004/080172 teaches to combine 4-benzoyl substituted 5-hydroxypyrazole compounds including topramezone with a safening amount of cloquintocet or its environmentally acceptable salts, esters, amides or hydrates.

Pinoxaden (IUPAC: 8-(2,6-diethyl-p-tolyl)-1,2,4,5-tetrahydro-7-oxo-7H-pyrazolo[1,2-d][1,4,5]oxadiazepin-9-yl 2,2-dimethylpropionate) is a well known herbicide active compounds (see C. D. S Tomlin (Ed.), The Pesticide Manual, 14th ed., 2006, BCPC Alton, Hampshire, UK, pp. 843 f.). Pinoxaden is known to be an inhibitor of fatty acid synthesis (ACCase inhibitor) and provides post emergence control of annual grasses such as *Alopecurus-*, *Apera-*, *Avena-*, *Lolium*, *Phalaris* and *Setaria* species in wheat and barley. Pinoxaden is marketed by Syngenta as a co-formulation with cloquintocet-mexyl under the tradename Axial®.

WO 2007/073933 teaches EC coformulations of pinoxaden with cloquintocet-mexyl containing an alcohol as adjuvant.

WO 2008/049618 teaches EC coformulations of pinoxaden with cloquintocet-mexyl and a further herbicide such as clodinafop or florasulam containing a triphosphate as an adjuvant.

SUMMARY OF THE INVENTION

It is an object of the present invention to provide herbicidal compositions, which show enhanced herbicide action against undesirable harmful plants and/or to improve the compatibility with crop plants, in particular improved compatibility with small-grain cereal crops such as, for example, wheat, durum, triticale, rye and barley. The composition should have a good post-emergence herbicidal activity against harmful plants.

We have found that these and further objects are achieved, surprisingly, by herbicidally active compositions comprising
a) a herbicide compound A which is selected from topramezone, the salts and esters, carbonates or thiocarbonates thereof; and
b) a second herbicide compound B which is pinoxaden.

The composition of the invention may further comprise a herbicide safener compound C.

The composition of the invention may further comprise a further herbicide compound D, which is different from the herbicide compounds A and B.

The invention furthermore relates to the use of a composition as defined herein for controlling undesirable vegetation in crops and non-crop areas. When using the compositions of the invention for this purpose the herbicide compound A and pinoxaden (hereinafter also termed herbicide (compound) B) and, if present, the herbicide safener component C (as defined hereinafter) and/or the further herbicide compound D (as defined hereinafter) can be applied simultaneously or in succession to the areas, where undesirable vegetation occurs or may occur. The compounds A and B and optionally C and/or D are in particular applied in crops, where undesirable vegetation may occur.

The invention furthermore relates to the use of a composition as defined herein for controlling undesirable vegetation in crops which, by genetic engineering or by breeding, are resistant to one or more herbicides and/or pathogens such as harmful fungi, and/or to attack by insects; preferably resistant to one or more synthetic of the following herbicides: 4-HPPD inhibitor herbicides, ACCase inhibitor herbicides, one or more of the herbicide compounds D mentioned below, namely against inhibitors of photosynthesis, in particular inhibitors of photosynthesis at photosystem II, against inhibitors of protoporphyrinogen-IX-oxidase, against acetolactate synthase (ALS) inhibitors, in particular imidazolinones, against bleacher herbicides or against auxinic herbicides.

The invention furthermore relates to a method for controlling undesirable vegetation, which comprises applying a herbicidal composition according to the present invention to the undesirable plants. Application can be done before, during and/or after, preferably during and/or after, in particular after the emergence of the undesirable plants. The herbicide compound A and pinoxaden, and, if present, the herbicide safener component C and/or the herbicide compound D can be applied simultaneously or in succession.

The invention in particular relates to a method for controlling undesirable vegetation in crops, which comprises applying an herbicidal composition according to the present invention in crops where undesirable vegetation occurs or might occur.

The invention furthermore relates to a method for controlling undesirable vegetation, which comprises allowing a composition according to the present invention to act on plants, their habitat or on seed.

In the methods of the present invention it is immaterial whether the herbicide compound A, pinoxaden and, if present, a herbicide safener component C and/or the herbicide compound D are formulated and applied jointly or separately. In the case of separate application it is of minor importance, in which order the application takes place. It is only necessary, that the herbicide compound A and the herbicide compound B and, if present, the herbicide safener compound C and/or the further herbicide compound D are applied in a time frame that allows simultaneous action of the active ingredients on the plants, preferably within a time-frame of at most 14 days, in particular at most 7 days.

The invention also relates to an herbicide formulation, which comprises a herbicidally active composition as defined herein and at least one carrier material, including liquid and/or solid carrier materials.

DETAILED DESCRIPTION OF THE INVENTION

Surprisingly, the compositions according to the present invention have better herbicidal activity against harmful plants than would have been expected by the herbicidal activity of the individual compounds. In other words, the joint action of topramezone, a salt or ester thereof and pinoxaden results in an enhanced activity against harmful plants in the sense of a synergy effect (synergism or potentiation), even at low application rates of topramezone. For this reason, the compositions can, based on the individual components, be used at lower application rates to achieve a herbicidal effect comparable to the individual components.

Moreover, the compositions of the present invention provide good pre- and post-emergence herbicidal activity; in particular, the compositions are useful for combating/controlling harmful plants after their emergence (post-emergence). The compositions of the present invention also show good crop compatibility, i.e. their use in crops does not result in increased damage when compared to the individual application of topramezone or pinoxaden.

As used herein, the terms "controlling" and "combating" are synonyms.

As used herein, the terms "undesirable vegetation" and "harmful plants" are synonyms.

The compositions of the invention may contain topramezone as such. As the OH group in pyrazole moiety of topramezone is acidic, the composition may also contain a salt of topramezone, in particular an alkalimetal salt or an ammonium salt as defined below for the herbicide safener compound C and or the herbicide compound D. The OH group of topramezone may also be present in esterified form, e.g. in the form of an $C_1$-$C_4$-alkylcarbonyloxy group or in the form of a carbonate or thiocarbonate group, e.g. in the form of a $C_1$-$C_4$-alkylcarbonate or $C_1$-$C_4$-alkylthiocarbonate group. Usually, the compositions of the invention contain topramezone as such or a salt of topramezone, in particular an alkalimetal salt or an ammonium salt as defined below.

If the compounds mentioned as herbicide compounds D and safeners C have functional groups, which can be ionized, they can also be used in the form of their agriculturally acceptable salts.

In general, the salts of those cations are suitable whose cations have no adverse effect on the action of the active compounds ("agriculturally acceptable").

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_8$-alkyl, $C_1$-$C_4$-alkyl, hydroxy-$C_1$-$C_4$-alkyl, in particular hydroxy-$C_2$-$C_4$-alkyl, $C_1$-$C_4$-alkoxy-$C_1$-$C_4$-alkyl, in particular $C_1$-$C_4$-alkoxy-$C_2$-$C_4$-alkyl, hydroxy-$C_1$-$C_4$-alkoxy-$C_1$-$C_4$-alkyl, in particular hydroxy-$C_2$-$C_4$-alkoxy-$C_2$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, pentylammonium, hexylammonium, heptylammonium, 2-hydroxyethylammonium (olamine salt), 2-(2-hydroxyethoxy)eth-1-ylammonium (diglycolamine salt), di(2-hydroxyeth-1-yl)ammonium (=diethanolammonium salt or diolamine salt), tri(2-hydroxyethyl)ammonium (=triethanolammonium salt or trolamine salt), mono-, di- and tri(hydroxypropyl)ammonium (=mono-, di- and tripropanolammonium), benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

In the compositions according to the invention, the compounds that carry a carboxyl group can also be employed in the form of agriculturally acceptable derivatives, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl (butoyl) esters. An example of the straight-chain or branched $C_1$-$C_{10}$-alkyl thioesters is the ethyl thioester. Preferred derivatives are the esters.

In the compositions of the present invention the relative weight ratio of herbicide compound A, calculated as topramezone, to pinoxaden, is preferably in the range from 1:1 to 1:15, in particular from 1:2 to 1:6. Accordingly, in the methods and uses of the invention, topramezone and pinoxaden are preferably applied within these weight ratios.

The compositions of the invention may also comprise, as a component C, one or more herbicide safeners. Herbicide safeners, also termed as safeners, are organic compounds which in some cases lead to better crop plant compatibility when applied jointly with specifically acting herbicides. Some safeners are themselves herbicidally active. In these cases, the safeners act as antidote or antagonist in the crop plants and thus reduce or even prevent damage to the crop plants. In a preferred embodiment of the invention, the composition contains at least one safener in an effective amount, which is generally at least 0.1% by weight, in particular at least 0.2 or at least 0.5% by weight, based on the total amount of herbicide compound A, pinoxaden and, if present, herbicide compound D. In this preferred embodiment, the weight ratio of the herbicide compound A and the herbicide safener compound C is generally from 2:1 to 1:15, in particular from 1:1 to 1:7 wherein the herbicide compound A is calculated as topramezone. In this preferred embodiment, the weight ratio of the herbicide compound A and pinoxaden is preferably in the range from 1:1 to 1:15, in particular from 1:2 to 1:6. In this preferred embodiment, the weight ratio of the total amounts of herbicide compound A plus pinoxaden to the amount of the herbicide safener compound C is generally from 6:1 to 1:6, in particular from 3:1 to 1:3 wherein the herbicide compound A is calculated as topramezone.

Suitable safeners, which can be used in the compositions according to the present invention are known in the art, e.g. from
The Compendium of Pesticide Common Names (http://www.alanwood.net/pesticides/);
Farm Chemicals Handbook 2000 Vol. 86, Meister Publishing Company, 2000;
B. Hock, C. Fedtke, R. R. Schmidt, Herbizide, Georg Thieme Verlag, Stuttgart 1995;
W. H. Ahrens, Herbicide Handbook, 7th Edition, Weed Science Society of America, 1994; and
K. K. Hatzios, Herbicide Handbook, Supplement to $7^{th}$ Edition, Weed Science Society of America, 1998.

Safeners include benoxacor, cloquintocet, cyometrinil, cyprosulfamide, dichlormid, dicyclonon, diethotate, fenchlorazole, fenclorim, flurazole, fluxofenim, furilazole, isoxadifen, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil, as well as the agriculturally acceptable salts thereof and, provided they have a carboxyl group, their agriculturally acceptable derivatives, in particular their esters. Safeners also include N-(2-methoxybenzoyl)-4-[(methylaminocarbonyl)amino]benzenesulfonamide [CAS 129531-12-0]. 2,2,5-Trimethyl-3-(dichloroacetyl)-1,3-oxazolidine [CAS No. 52836-31-4] is also known under the name R-29148.4-(Dichloroacetyl)-1-oxa-4-azaspiro[4.5]decane [CAS No. 71526-07-03] is also known under the names AD-67 and MON 4660.

As safener, the compositions according to the invention preferably comprise at least one of the compounds selected from the group of mefenpyr, isoxadifen, cloquintocet, the salts and esters of the aforementioned compounds. Likewise, as safener, the compositions according to the invention preferably comprise at least one of the compounds selected from the group of cyprosulfamide and N-(2-methoxybenzoyl)-4-[(methylaminocarbonyl)amino]benzenesulfonamide.

In a particular preferred embodiment of the invention, the compositions of the invention comprise as a safener cloquintocet, a salt thereof or an ester thereof, e.g. cloquintocet-mexyl.

In another particular preferred embodiment of the invention, the compositions of the invention comprise as a safener isoxadifen, a salt thereof or an ester thereof, e.g. isoxadifen-ethyl.

In a further particular preferred embodiment of the invention, the compositions of the invention comprise as a safener mefenpyr, a salt thereof or an ester thereof, e.g. mefenpyr-diethyl.

In a further particular preferred embodiment of the invention, the compositions of the invention comprise as a safener cyprosulfamide.

In a further particular preferred embodiment of the invention, the compositions of the invention comprise as a safener N-(2-methoxybenzoyl)-4-[(methylaminocarbonyl)-amino] benzenesulfonamide.

If the compositions of the invention comprise a further herbicide component D, the relative weight ratio of herbicide compound A, calculated as topramezone, to the total amount of herbicide compounds B and D, is preferably from 1:1 to 1:500, in particular from 1:1 to 1:100, wherein each herbicide compound D, which is an ester or a salt of an acid is calculated as the acid. In these compositions, the weight ratio of herbicide compound B to herbicide compound D is preferably from 10:1 to 1:100, in particular from 10:1 to 1:20. In this embodiment the weight ratio of herbicide A and safener C is as defined above. Accordingly, in the methods and uses of the invention, topramezone, pinoxaden and the herbicide compounds D and safener C are preferably applied within these weight ratios.

According to a particular preferred embodiment (embodiment 1), the composition of the invention comprises topramezone, a salt or an ester, carbonate or thiocarbonate thereof, in particular topramezone as herbicide compound A, pinoxaden as herbicide compound B and cloquintocet, a salt or an ester thereof, in particular an ester of cloquintocet, such as cloquintocet-mexyl as herbicide safener C. In this embodiment, the weight ratios of topramezone to pinoxaden, the weight ratio of topramezone to cloquintocet (or an ester or salt thereof) and the weight ratio of the total amount of topramezone plus pinoxaden to cloquintocet (or an ester or salt thereof) is as given above for the weight ratio of the herbicide compounds A and B and herbicide safeners.

In addition to the herbicide compound A and pinoxaden and the optional safener C, the composition of the invention may contain one or more further herbicide compounds D. These further herbicide compounds D are usually selected from the following groups D.1 to D.6 of herbicide compounds:
D.1 synthetic lipid biosynthesis inhibitors;
D.2 acetolactate synthase inhibitors;
D.3 photosynthesis inhibitors;
D.4 protoporphyrinogen-IX-oxidase inhibitors;
D.5 bleacher herbicides; and
D.6 auxinic herbicides.

Compounds of the group of synthetic lipid biosynthesis inhibitors (group D.1) include in particular those herbicide compounds which are inhibitors of acetyl-CoA carboxylase (hereinafter termed ACCase inhibitors or ACC herbicides) and which belong to the group A of the HRAC classification system. Preferred herbicide compounds of this group D.1 are selected from the group consisting of clodinafop, diclofop, fenoxaprop, fenoxaprop-P and tralkoxydim and, where applicable, the salts and esters thereof, such as clodinafop-propargyl, diclofop-methyl, fenoxaprop-ethyl, fenoxaprop-P-ethyl.

Compounds of the group of acetolactate synthase inhibitors (group D.2, hereinafter also termed ALS-inhibitors) belong to the group B of the HRAC classification system. Preferred herbicide compounds of this group are selected from the group of sulfonylureas, such as amidosulfuron, chlorsulfuron, flucetosulfuron, flupyrsulfuron, iodosulfuron, mesosulfuron, metazosulfuron, metsulfuron, prosulfuron, sulfosulfuron, thifensulfuron, triasulfuron, tribenuron or tritosulfuron; imidazolinones, such as imazamox, imazapic, imazapyr, imazaquin or imazethapyr; triazolopyrimidine herbicides such as florasulam or pyroxsulam; triazolone herbicides such as flucarbazone, propoxycarbazone or thiencarbazone, and pyrimisulfan, and, where applicable, the salts and esters thereof such as mesosulfuron-methyl, metsulfuron-methyl, thifensulfuron-methyl, tribenuron-methyl, thiencarbazone-methyl and the like. Preferred compounds of the group D.2 are amidosulfuron, chlorsulfuron, florasulam, flucarbazone, flucetosulfuron, flupyrsulfuron, imazamox, iodosulfuron, mesosulfuron-methyl, metazosulfuron, metsulfuron-methyl, propoxycarbazone, prosulfuron, pyrimisulfan, pyroxsulam, sulfosulfuron, thiencarbazone, thifensulfuron-methyl, triasulfuron, tribenuron-methyl, tritosulfuron and, where applicable, the salts and esters thereof. Particular preferred compounds of the group B.2 are selected from the group consisting of amidosulfuron, chlorsulfuron, florasulam, flucetosulfuron, flupyrsulfuron, imazamox, metazosulfuron, metsulfuron-methyl, prosulfuron, pyrimisulfan, sulfosulfuron, thiencarbazone, thifensulfuron-methyl, triasulfuron, tribenuron-methyl and tritosulfuron and, where applicable, the salts thereof.

Compounds of the group of photosynthesis inhibitors (group D.3) include in particular those herbicide compounds which are inhibitors of photosynthesis at photosystem II (hereinafter termed PSII inhibitors) and which belong to the groups C1 to C3 of the HRAC classification system. Preferred herbicide compounds of this group D.3 belong to the group C3 of the HRAC classification system and are in particular selected from the group consisting of bentazone, bromoxynil, ioxynil and, where applicable, the salts and esters thereof.

Compounds of the group of protoporphyrinogen-IX-oxidase inhibitors (group D.4, hereinafter also termed as protox inhibitors) belong to the group E of the HRAC classification system. Preferred herbicide compounds of this group are selected from the group of bencarbazone, carfentrazone, cinidon-ethyl, pyraflufen and, where applicable, the salts and esters thereof such as carfentrazone-ethyl or pyraflufen-ethyl.

Compounds of the group of bleacher herbicides (group D.5) belong to the group F1 to F3 of the HRAC classification system. Preferred herbicide compounds of this group D5 are in particular selected from the group consisting of picolinafen and pyrasulfotole, and, where applicable, the salts thereof.

Compounds of the group of the auxinic herbicides (group D.6, hereinafter also termed synthetic auxins) have an action like indole acetic acid and belong to the group O of the HRAC classification system. Examples of herbicide compounds of this group include:

D.6.1 benzoic acid herbicides, such as dicamba, tricamba, chloramben or 2,3,6-TBA (2,3,6-trichlorobenzoic acid) and the salts and esters thereof;

D.6.2 pyridinecarboxylic acid herbicides, in particular aminopyralid, clopyralid, picloram, triclopyr or fluoroxypyr and the salts and esters thereof as mentioned above;

D.6.3 aminocyclopyrachlor, the salts and esters thereof as mentioned above; and

D.6.4 phenoxycarboxylic acid herbicides, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, MCPP (mecoprop), MCPP-P, and phenoxybutyric acid herbicides such as 4-CPB, 2,4-DB, 3,4-DB, 2,4,5-TB, MCPB, their salts and their esters, in particular one of the following phenoxycarboxylic acid herbicides: 2,4-D, 2,4-DB, 2,4-DP (dichlorprop), 2,4-DP-P, MCPP (mecoprop), MCPP-P, MCPA, MCPB, their salts and their esters.

Preferred compound of this group are selected from the group consisting of aminocyclopyrachlor, 2,4-D, 2,4-DB, 2,4-DP, 2,4-DP-P, clopyralid, dicamba, fluoroxypyr, MCPA, MCPB, MCPP, MCPP-P and, where applicable, the salts and esters thereof, such as aminocyclopyrachlor-potassium, aminocyclopyrachlor-methyl, 2,4-D-ammonium, 2,4-D-butotyl, 2,4-D-2-butoxypropyl, 2,4-D-3-butoxypropyl, 2,4-D-butyl, 2,4-D-diethylammonium, 2,4-D-dimethylammonium, 2,4-D-diolamine, 2,4-D-dodecylammonium, 2,4-D-ethyl, 2,4-D-2-ethylhexyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris (2-hydroxypropyl)ammonium, 2,4-D-trolamine, MCPA-butotyl, MCPA-butyl, MCPA-dimethylammonium, MCPA-diolamine, MCPA-ethyl, MCPA-2-ethylhexyl, MCPA-isobutyl, MCPA-isoctyl, MCPA-isopropyl, MCPA-methyl, MCPA-olamine, MCPA-potassium, MCPA-sodium, MCPA-trolamine, dichlorprop-butotyl, dichlorpropdimethylammonium, dichlorprop-ethylammonium, dichlorprop-2-ethylhexyl, dichlorpropisoctyl, dichlorprop-methyl, dichlorprop-potassium, dichlorprop-sodium, diclorop-P-dimethylammonium, mecoprop-dimethylammonium, mecoprop-diolamine, mecopropethadyl, mecoprop-isoctyl, mecoprop-methyl, mecoprop-potassium, mecoprop-sodium, mecoprop-trolamine, mecoprop-P-dimethylammonium, mecoprop-P-isobutyl, mecoprop-P-potassium, MCPB-methyl, MCPB-ethyl and MCPB-sodium. Particular preferred compound of this group are selected from the group consisting of aminocyclopyrachlor, 2,4-D, 2,4-DB, 2,4-DP, 2,4-DP-P, clopyralid, dicamba, fluoroxypyr, MCPA, MCPB, MCPP, MCPP-P and, where applicable, the salts and esters thereof.

In a first particular embodiment of the invention (embodiment 1a), the composition comprises the herbicide compound A, in particular topramezone, pinoxaden and a safener C as defined above, preferably a safener selected from the group consisting of mefenpyr, isoxadifen, cloquintocet, the salts and esters of the aforementioned compounds, in particular the safener cloquintocet, a salt of cloquintocet or an ester of cloquintocet such as cloquintocet-mexyl and no further herbicide compound D. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and no further herbicide compound D.

In a second particular embodiment of the invention, the composition comprises the herbicide compound A, in particular topramezone, pinoxaden, a safener C as defined above, preferably a safener selected from the group consisting of mefenpyr, isoxadifen, cloquintocet, the salts and esters of the aforementioned compounds, and a herbicide compound of group D.1 as defined above, which is preferably selected from the group consisting of clodinafop, diclofop, fenoxaprop, fenoxaprop-P and tralkoxydim and, where applicable, the salts and esters thereof, such as clodinafop-propargyl, diclofop-methyl, fenoxaprop-ethyl, fenoxaprop-P-ethyl. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and a herbicide compound of group D.1 as defined above, which is preferably selected from the group consisting of clodinafop, diclofop, fenoxaprop, fenoxaprop-P and tralkoxydim and, where applicable, the salts and esters thereof, such as clodinafop-propargyl, diclofop-methyl, fenoxaprop-ethyl, fenoxaprop-P-ethyl.

In a third particular embodiment of the invention, the composition comprises the herbicide compound A, in particular topramezone, pinoxaden, a safener C as defined above, preferably a safener selected from the group consisting of mefenpyr, isoxadifen, cloquintocet, the salts and esters of the aforementioned compounds, and a herbicide compound of group D.2 as defined above, which is preferably selected from the group consisting of amidosulfuron, chlorsulfuron, florasulam, flucarbazone, flucetosulfuron, flupyrsulfuron, imazamox, iodosulfuron, mesosulfuron-methyl, metazosulfuron, metsulfuron-methyl, propoxycarbazone, prosulfuron, pyrimisulfan, pyroxsulam, sulfosulfuron, thiencarbazone, thifensulfuron-methyl, triasulfuron, tribenuron-methyl, tritosulfuron and, where applicable, the salts and esters thereof and which is in particular selected from the group consisting of amidosulfuron, chlorsulfuron, florasulam, flucetosulfuron, flupyrsulfuron, imazamox, metazosulfuron, metsulfuron-methyl, prosulfuron, pyrimisulfan, sulfosulfuron, thiencarbazone, thiencarbazone-methyl, thifensulfuron-methyl, triasulfuron, tribenuron-methyl and tritosulfuron and, where applicable, the salts thereof. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and a herbicide compound of group D.2 as defined above, which is preferably selected from the group consisting of amidosulfuron, chlorsulfuron, florasulam, flucarbazone, flucetosulfuron, flupyrsulfuron, imazamox, iodosulfuron, mesosulfuron-methyl, metazosulfuron, metsulfuron-methyl, propoxycarbazone, prosulfuron, pyrimisulfan, pyroxsulam, sulfosulfuron, thiencarbazone, thifensulfuron-methyl, triasulfuron, tribenuron-methyl, tritosulfuron and, where applicable, the salts and esters thereof and which is in particular selected from the group consisting of amidosulfuron, chlorsulfuron, florasulam, flucetosulfuron, flupyrsulfuron, imazamox, metazosulfuron, metsulfuron-methyl, prosulfuron, pyrimisulfan, sulfosulfuron, thiencarbazone, thiencarbazone-methyl, thifensulfuron-methyl, triasulfuron, tribenuron-methyl and tritosulfuron and, where applicable, the salts thereof.

In a fourth particular embodiment of the invention, the composition comprises the herbicide compound A, in particular topramezone, pinoxaden, a safener C as defined above, preferably a safener selected from the group consisting of mefenpyr, isoxadifen, cloquintocet, the salts and esters of the aforementioned compounds, and a herbicide compound of group D.3 as defined above, which is preferably selected from the group consisting of bentazone, bromoxynil, ioxynil and, where applicable, the salts and esters thereof. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and a herbicide compound of group D.3 as defined above, which is preferably selected from the group consisting of bentazone, bromoxynil, ioxynil and, where applicable, the salts and esters thereof.

In a fifth particular embodiment of the invention, the composition comprises the herbicide compound A, in particular topramezone, pinoxaden, a safener C as defined above, preferably a safener selected from the group consisting of mefenpyr, isoxadifen, cloquintocet, the salts and esters of the aforementioned compounds, and a herbicide compound of group D.4 as defined above, which is preferably selected from the group consisting of bencarbazone, carfentrazone, cinidon-ethyl, pyraflufen, and where applicable, the salts and esters thereof, such as carfentrazone-ethyl. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and a herbicide compound of group D.4 as defined above, which is preferably selected from the group consisting of bencarbazone, carfentrazone, cinidon-ethyl, pyraflufen, and where applicable, the salts and esters thereof, such as carfentrazone-ethyl.

In a sixth particular embodiment of the invention, the composition comprises the herbicide compound A, in particular topramezone, pinoxaden, a safener C as defined above, preferably a safener selected from the group consisting of mefenpyr, isoxadifen, cloquintocet, the salts and esters of the aforementioned compounds, and a herbicide compound of group D.5 as defined above, which is preferably selected from the group consisting of picolinafen and pyrasulfotole, and, where applicable, the salts thereof. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and a herbicide compound of group D.5 as defined above, which is preferably selected from the group consisting of picolinafen and pyrasulfotole, and, where applicable, the salts thereof.

In a seventh particular embodiment of the invention, the composition comprises the herbicide compound A, in particular topramezone, pinoxaden, a safener C as defined above, preferably a safener selected from the group consisting of mefenpyr, isoxadifen, cloquintocet, the salts and esters of the aforementioned compounds, and a herbicide compound of group D.6 as defined above, which is preferably selected from the group consisting of the compounds mentioned in the groups D.6.1, D.6.2, D.6.3 and D.6.4 and which is in particular selected from the group consisting of aminocyclopyrachlor, 2,4-D, 2,4-DB, 2,4-DP, 2,4-DP-P, clopyralid, dicamba, fluoroxypyr, MCPA, MCPB, MCPP, MCPP-P and, where applicable, the salts and esters thereof. Preference is also given to those compositions containing the herbicide compound A, in particular topramezone, pinoxaden and a safener C selected from cyprosulfamide and N-(2-methoxybenzoyl)-4-[(methylaminocarbonyl)amino]benzenesulfonamide and a herbicide compound of group D.6 as defined above, which is preferably selected from the group consisting of the compounds mentioned in the groups D.6.1, D.6.2, D.6.3 and D.6.4 and which is in particular selected from the group consisting of aminocyclopyrachlor, 2,4-D, 2,4-DB, 2,4-DP, 2,4-DP-P, clopyralid, dicamba, fluoroxypyr, MCPA, MCPB, MCPP, MCPP-P and, where applicable, the salts and esters thereof.

In the compositions according to the first to seventh particular embodiment, the weight ratios of the compounds A, B, C and D are as defined above.

In the compositions according to the first to seventh particular embodiment, the herbicide compound A is preferably topramezone or a salt thereof, in particular topramezone.

In the compositions according to the first to seventh particular embodiment, the safener C is preferably cloquintocet, a salt or an ester thereof, in particular an ester of cloquintocet, such as cloquintocet-mexyl.

Particular preferred examples of compositions according to the invention are given in the following table A. In the compositions according to table A, the weight ratios of the compounds A, B, C and D are as defined above.

TABLE A

| # | Compound A | Compound B | Compound C | Compound D |
|---|---|---|---|---|
| 1 | topramezone | pinoxaden | cloquintocet-mexyl | — |
| 2 | topramezone | pinoxaden | cloquintocet-mexyl | diclofop |
| 3 | topramezone | pinoxaden | cloquintocet-mexyl | diclofop-methyl |
| 4 | topramezone | pinoxaden | cloquintocet-mexyl | clodinafop |
| 5 | topramezone | pinoxaden | cloquintocet-mexyl | clodinafop-propargyl |
| 6 | topramezone | pinoxaden | cloquintocet-mexyl | fenoxaprop |
| 7 | topramezone | pinoxaden | cloquintocet-mexyl | fenoxaprop-ethyl |
| 8 | topramezone | pinoxaden | cloquintocet-mexyl | fenoxaprop-P |
| 9 | topramezone | pinoxaden | cloquintocet-mexyl | fenoxaprop-P-ethyl |
| 10 | topramezone | pinoxaden | cloquintocet-mexyl | tralkoxydim |
| 11 | topramezone | pinoxaden | cloquintocet-mexyl | amidosulfuron |
| 12 | topramezone | pinoxaden | cloquintocet-mexyl | chlorsulfuron |
| 13 | topramezone | pinoxaden | cloquintocet-mexyl | florasulam |
| 14 | topramezone | pinoxaden | cloquintocet-mexyl | flucarbazone |
| 15 | topramezone | pinoxaden | cloquintocet-mexyl | flucetosulfuron |

TABLE A-continued

| # | Compound A | Compound B | Compound C | Compound D |
|---|---|---|---|---|
| 16 | topramezone | pinoxaden | cloquintocet-mexyl | flupyrsulfuron |
| 17 | topramezone | pinoxaden | cloquintocet-mexyl | imazamox* |
| 18 | topramezone | pinoxaden | cloquintocet-mexyl | iodosulfuron |
| 19 | topramezone | pinoxaden | cloquintocet-mexyl | iodosulfuron-methyl-sodium |
| 20 | topramezone | pinoxaden | cloquintocet-mexyl | mesosulfuron-methyl |
| 21 | topramezone | pinoxaden | cloquintocet-mexyl | metazosulfuron |
| 22 | topramezone | pinoxaden | cloquintocet-mexyl | metsulfuron-methyl |
| 23 | topramezone | pinoxaden | cloquintocet-mexyl | propoxycarbazone* |
| 24 | topramezone | pinoxaden | cloquintocet-mexyl | prosulfuron |
| 25 | topramezone | pinoxaden | cloquintocet-mexyl | pyrimisulfan |
| 26 | topramezone | pinoxaden | cloquintocet-mexyl | pyroxsulam |
| 27 | topramezone | pinoxaden | cloquintocet-mexyl | sulfosulfuron |
| 28 | topramezone | pinoxaden | cloquintocet-mexyl | thiencarbazone |
| 29 | topramezone | pinoxaden | cloquintocet-mexyl | thiencarbazone-methyl |
| 30 | topramezone | pinoxaden | cloquintocet-mexyl | thifensulfuron-methyl |
| 31 | topramezone | pinoxaden | cloquintocet-mexyl | triasulfuron |
| 32 | topramezone | pinoxaden | cloquintocet-mexyl | tribenuron-methyl |
| 33 | topramezone | pinoxaden | cloquintocet-mexyl | tritosulfuron |
| 34 | topramezone | pinoxaden | cloquintocet-mexyl | bentazone |
| 35 | topramezone | pinoxaden | cloquintocet-mexyl | bentazone-sodium |
| 36 | topramezone | pinoxaden | cloquintocet-mexyl | bromoxynil |
| 37 | topramezone | pinoxaden | cloquintocet-mexyl | ioxynil |
| 38 | topramezone | pinoxaden | cloquintocet-mexyl | bencarbazone |
| 39 | topramezone | pinoxaden | cloquintocet-mexyl | carfentrazone |
| 40 | topramezone | pinoxaden | cloquintocet-mexyl | carfentrazone-ethyl |
| 41 | topramezone | pinoxaden | cloquintocet-mexyl | cinidon-ethyl |
| 42 | topramezone | pinoxaden | cloquintocet-mexyl | pyraflufen |
| 43 | topramezone | pinoxaden | cloquintocet-mexyl | pyraflufen-ethyl |
| 44 | topramezone | pinoxaden | cloquintocet-mexyl | picolinafen |
| 45 | topramezone | pinoxaden | cloquintocet-mexyl | pyrasulfotole |
| 46 | topramezone | pinoxaden | cloquintocet-mexyl | amino-cyclopyrachlor* |
| 47 | topramezone | pinoxaden | cloquintocet-mexyl | 2,4-D* |
| 48 | topramezone | pinoxaden | cloquintocet-mexyl | 2,4-DB* |
| 49 | topramezone | pinoxaden | cloquintocet-mexyl | 2,4-DP* |
| 50 | topramezone | pinoxaden | cloquintocet-mexyl | 2,4-DP-P* |
| 51 | topramezone | pinoxaden | cloquintocet-mexyl | clopyralid* |
| 52 | topramezone | pinoxaden | cloquintocet-mexyl | dicamba* |
| 53 | topramezone | pinoxaden | cloquintocet-mexyl | fluroxypyr** |
| 54 | topramezone | pinoxaden | cloquintocet-mexyl | MCPA* |
| 55 | topramezone | pinoxaden | cloquintocet-mexyl | MCPB* |
| 56 | topramezone | pinoxaden | cloquintocet-mexyl | MCPP* |
| 57 | topramezone | pinoxaden | cloquintocet-mexyl | MCPP-P* |
| 58 | topramezone | pinoxaden | mefenpyr-diethyl | — |
| 59 | topramezone | pinoxaden | mefenpyr-diethyl | diclofop |
| 60 | topramezone | pinoxaden | mefenpyr-diethyl | diclofop-methyl |
| 61 | topramezone | pinoxaden | mefenpyr-diethyl | clodinafop |
| 62 | topramezone | pinoxaden | mefenpyr-diethyl | clodinafop-propargyl |
| 63 | topramezone | pinoxaden | mefenpyr-diethyl | fenoxaprop |
| 64 | topramezone | pinoxaden | mefenpyr-diethyl | fenoxaprop-ethyl |
| 65 | topramezone | pinoxaden | mefenpyr-diethyl | fenoxaprop-P |
| 66 | topramezone | pinoxaden | mefenpyr-diethyl | fenoxaprop-P-ethyl |
| 67 | topramezone | pinoxaden | mefenpyr-diethyl | tralkoxydim |
| 68 | topramezone | pinoxaden | mefenpyr-diethyl | amidosulfuron |
| 69 | topramezone | pinoxaden | mefenpyr-diethyl | chlorsulfuron |
| 70 | topramezone | pinoxaden | mefenpyr-diethyl | florasulam |
| 71 | topramezone | pinoxaden | mefenpyr-diethyl | flucarbazone |
| 72 | topramezone | pinoxaden | mefenpyr-diethyl | flucetosulfuron |
| 73 | topramezone | pinoxaden | mefenpyr-diethyl | flupyrsulfuron |
| 74 | topramezone | pinoxaden | mefenpyr-diethyl | imazamox* |
| 75 | topramezone | pinoxaden | mefenpyr-diethyl | iodosulfuron |
| 76 | topramezone | pinoxaden | mefenpyr-diethyl | iodosulfuron-methyl-sodium |
| 77 | topramezone | pinoxaden | mefenpyr-diethyl | mesosulfuron-methyl |
| 78 | topramezone | pinoxaden | mefenpyr-diethyl | metazosulfuron |
| 79 | topramezone | pinoxaden | mefenpyr-diethyl | metsulfuron-methyl |
| 80 | topramezone | pinoxaden | mefenpyr-diethyl | propoxycarbazone* |
| 81 | topramezone | pinoxaden | mefenpyr-diethyl | prosulfuron |
| 82 | topramezone | pinoxaden | mefenpyr-diethyl | pyrimisulfan |
| 83 | topramezone | pinoxaden | mefenpyr-diethyl | pyroxsulam |
| 84 | topramezone | pinoxaden | mefenpyr-diethyl | sulfosulfuron |
| 85 | topramezone | pinoxaden | mefenpyr-diethyl | thiencarbazone |
| 86 | topramezone | pinoxaden | mefenpyr-diethyl | thiencarbazone-methyl |
| 87 | topramezone | pinoxaden | mefenpyr-diethyl | thifensulfuron-methyl |
| 88 | topramezone | pinoxaden | mefenpyr-diethyl | triasulfuron |
| 89 | topramezone | pinoxaden | mefenpyr-diethyl | tribenuron-methyl |
| 90 | topramezone | pinoxaden | mefenpyr-diethyl | tritosulfuron |
| 91 | topramezone | pinoxaden | mefenpyr-diethyl | bentazone |
| 92 | topramezone | pinoxaden | mefenpyr-diethyl | bentazone-sodium |
| 93 | topramezone | pinoxaden | mefenpyr-diethyl | bromoxynil |
| 94 | topramezone | pinoxaden | mefenpyr-diethyl | ioxynil |
| 95 | topramezone | pinoxaden | mefenpyr-diethyl | bencarbazone |
| 96 | topramezone | pinoxaden | mefenpyr-diethyl | carfentrazone |
| 97 | topramezone | pinoxaden | mefenpyr-diethyl | carfentrazone-ethyl |
| 98 | topramezone | pinoxaden | mefenpyr-diethyl | cinidon-ethyl |
| 99 | topramezone | pinoxaden | mefenpyr-diethyl | pyraflufen |
| 100 | topramezone | pinoxaden | mefenpyr-diethyl | pyraflufen-ethyl |
| 101 | topramezone | pinoxaden | mefenpyr-diethyl | picolinafen |
| 102 | topramezone | pinoxaden | mefenpyr-diethyl | pyrasulfotole |
| 103 | topramezone | pinoxaden | mefenpyr-diethyl | amino-cyclopyrachlor* |
| 104 | topramezone | pinoxaden | mefenpyr-diethyl | 2,4-D* |
| 105 | topramezone | pinoxaden | mefenpyr-diethyl | 2,4-DB* |
| 106 | topramezone | pinoxaden | mefenpyr-diethyl | 2,4-DP* |
| 107 | topramezone | pinoxaden | mefenpyr-diethyl | 2,4-DP-P* |
| 108 | topramezone | pinoxaden | mefenpyr-diethyl | clopyralid* |
| 109 | topramezone | pinoxaden | mefenpyr-diethyl | dicamba* |
| 110 | topramezone | pinoxaden | mefenpyr-diethyl | fluroxypyr** |
| 111 | topramezone | pinoxaden | mefenpyr-diethyl | MCPA* |
| 112 | topramezone | pinoxaden | mefenpyr-diethyl | MCPB* |
| 113 | topramezone | pinoxaden | mefenpyr-diethyl | MCPP* |
| 114 | topramezone | pinoxaden | mefenpyr-diethyl | MCPP-P* |
| 115 | topramezone | pinoxaden | isoxadifen-ethyl | — |
| 116 | topramezone | pinoxaden | isoxadifen-ethyl | diclofop |
| 117 | topramezone | pinoxaden | isoxadifen-ethyl | diclofop-methyl |
| 118 | topramezone | pinoxaden | isoxadifen-ethyl | clodinafop |
| 119 | topramezone | pinoxaden | isoxadifen-ethyl | clodinafop-propargyl |
| 120 | topramezone | pinoxaden | isoxadifen-ethyl | fenoxaprop |
| 121 | topramezone | pinoxaden | isoxadifen-ethyl | fenoxaprop-ethyl |
| 122 | topramezone | pinoxaden | isoxadifen-ethyl | fenoxaprop-P |
| 123 | topramezone | pinoxaden | isoxadifen-ethyl | fenoxaprop-P-ethyl |
| 124 | topramezone | pinoxaden | isoxadifen-ethyl | tralkoxydim |
| 125 | topramezone | pinoxaden | isoxadifen-ethyl | amidosulfuron |
| 126 | topramezone | pinoxaden | isoxadifen-ethyl | chlorsulfuron |
| 127 | topramezone | pinoxaden | isoxadifen-ethyl | florasulam |
| 128 | topramezone | pinoxaden | isoxadifen-ethyl | flucarbazone |
| 129 | topramezone | pinoxaden | isoxadifen-ethyl | flucetosulfuron |
| 130 | topramezone | pinoxaden | isoxadifen-ethyl | flupyrsulfuron |
| 131 | topramezone | pinoxaden | isoxadifen-ethyl | imazamox* |
| 132 | topramezone | pinoxaden | isoxadifen-ethyl | iodosulfuron |
| 133 | topramezone | pinoxaden | isoxadifen-ethyl | iodosulfuron-methyl-sodium |
| 134 | topramezone | pinoxaden | isoxadifen-ethyl | mesosulfuron-methyl |
| 135 | topramezone | pinoxaden | isoxadifen-ethyl | metazosulfuron |
| 136 | topramezone | pinoxaden | isoxadifen-ethyl | metsulfuron-methyl |
| 137 | topramezone | pinoxaden | isoxadifen-ethyl | propoxycarbazone* |
| 138 | topramezone | pinoxaden | isoxadifen-ethyl | prosulfuron |
| 139 | topramezone | pinoxaden | isoxadifen-ethyl | pyrimisulfan |
| 140 | topramezone | pinoxaden | isoxadifen-ethyl | pyroxsulam |
| 141 | topramezone | pinoxaden | isoxadifen-ethyl | sulfosulfuron |
| 142 | topramezone | pinoxaden | isoxadifen-ethyl | thiencarbazone |
| 143 | topramezone | pinoxaden | isoxadifen-ethyl | thiencarbazone-methyl |
| 144 | topramezone | pinoxaden | isoxadifen-ethyl | thifensulfuron-methyl |
| 145 | topramezone | pinoxaden | isoxadifen-ethyl | triasulfuron |
| 146 | topramezone | pinoxaden | isoxadifen-ethyl | tribenuron-methyl |
| 147 | topramezone | pinoxaden | isoxadifen-ethyl | tritosulfuron |
| 148 | topramezone | pinoxaden | isoxadifen-ethyl | bentazone |
| 149 | topramezone | pinoxaden | isoxadifen-ethyl | bentazone-sodium |
| 150 | topramezone | pinoxaden | isoxadifen-ethyl | bromoxynil |
| 151 | topramezone | pinoxaden | isoxadifen-ethyl | ioxynil |
| 152 | topramezone | pinoxaden | isoxadifen-ethyl | bencarbazone |

TABLE A-continued

| # | Compound A | Compound B | Compound C | Compound D |
|---|---|---|---|---|
| 153 | topramezone | pinoxaden | isoxadifen-ethyl | carfentrazone |
| 154 | topramezone | pinoxaden | isoxadifen-ethyl | carfentrazone-ethyl |
| 155 | topramezone | pinoxaden | isoxadifen-ethyl | cinidon-ethyl |
| 156 | topramezone | pinoxaden | isoxadifen-ethyl | pyraflufen |
| 157 | topramezone | pinoxaden | isoxadifen-ethyl | pyraflufen-ethyl |
| 158 | topramezone | pinoxaden | isoxadifen-ethyl | picolinafen |
| 159 | topramezone | pinoxaden | isoxadifen-ethyl | pyrasulfotole |
| 160 | topramezone | pinoxaden | isoxadifen-ethyl | amino-cyclopyrachlor* |
| 161 | topramezone | pinoxaden | isoxadifen-ethyl | 2,4-D* |
| 162 | topramezone | pinoxaden | isoxadifen-ethyl | 2,4-DB* |
| 163 | topramezone | pinoxaden | isoxadifen-ethyl | 2,4-DP* |
| 164 | topramezone | pinoxaden | isoxadifen-ethyl | 2,4-DP-P* |
| 165 | topramezone | pinoxaden | isoxadifen-ethyl | clopyralid* |
| 166 | topramezone | pinoxaden | isoxadifen-ethyl | dicamba* |
| 167 | topramezone | pinoxaden | isoxadifen-ethyl | fluroxypyr** |
| 168 | topramezone | pinoxaden | isoxadifen-ethyl | MCPA* |
| 169 | topramezone | pinoxaden | isoxadifen-ethyl | MCPB* |
| 170 | topramezone | pinoxaden | isoxadifen-ethyl | MCPP* |
| 171 | topramezone | pinoxaden | isoxadifen-ethyl | MCPP-P* |
| 172 | topramezone | pinoxaden | cyprosulfamide | — |
| 173 | topramezone | pinoxaden | cyprosulfamide | diclofop |
| 174 | topramezone | pinoxaden | cyprosulfamide | diclofop-methyl |
| 175 | topramezone | pinoxaden | cyprosulfamide | clodinafop |
| 176 | topramezone | pinoxaden | cyprosulfamide | clodinafop-propargyl |
| 177 | topramezone | pinoxaden | cyprosulfamide | fenoxaprop |
| 178 | topramezone | pinoxaden | cyprosulfamide | fenoxaprop-ethyl |
| 179 | topramezone | pinoxaden | cyprosulfamide | fenoxaprop-P |
| 180 | topramezone | pinoxaden | cyprosulfamide | fenoxaprop-P-ethyl |
| 181 | topramezone | pinoxaden | cyprosulfamide | tralkoxydim |
| 182 | topramezone | pinoxaden | cyprosulfamide | amidosulfuron |
| 183 | topramezone | pinoxaden | cyprosulfamide | chlorsulfuron |
| 184 | topramezone | pinoxaden | cyprosulfamide | florasulam |
| 185 | topramezone | pinoxaden | cyprosulfamide | flucarbazone |
| 186 | topramezone | pinoxaden | cyprosulfamide | flucetosulfuron |
| 187 | topramezone | pinoxaden | cyprosulfamide | flupyrsulfuron |
| 188 | topramezone | pinoxaden | cyprosulfamide | imazamox* |
| 189 | topramezone | pinoxaden | cyprosulfamide | iodosulfuron |
| 190 | topramezone | pinoxaden | cyprosulfamide | iodosulfuron-methyl-sodium |
| 191 | topramezone | pinoxaden | cyprosulfamide | mesosulfuron-methyl |
| 192 | topramezone | pinoxaden | cyprosulfamide | metazosulfuron |
| 193 | topramezone | pinoxaden | cyprosulfamide | metsulfuron-methyl |
| 194 | topramezone | pinoxaden | cyprosulfamide | propoxycarbazone* |
| 195 | topramezone | pinoxaden | cyprosulfamide | prosulfuron |
| 196 | topramezone | pinoxaden | cyprosulfamide | pyrimisulfan |
| 197 | topramezone | pinoxaden | cyprosulfamide | pyroxsulam |
| 198 | topramezone | pinoxaden | cyprosulfamide | sulfosulfuron |
| 199 | topramezone | pinoxaden | cyprosulfamide | thiencarbazone |
| 200 | topramezone | pinoxaden | cyprosulfamide | thiencarbazone-methyl |
| 201 | topramezone | pinoxaden | cyprosulfamide | thifensulfuron-methyl |
| 202 | topramezone | pinoxaden | cyprosulfamide | triasulfuron |
| 203 | topramezone | pinoxaden | cyprosulfamide | tribenuron-methyl |
| 204 | topramezone | pinoxaden | cyprosulfamide | tritosulfuron |
| 205 | topramezone | pinoxaden | cyprosulfamide | bentazone |
| 206 | topramezone | pinoxaden | cyprosulfamide | bentazone-sodium |
| 207 | topramezone | pinoxaden | cyprosulfamide | bromoxynil |
| 208 | topramezone | pinoxaden | cyprosulfamide | ioxynil |
| 209 | topramezone | pinoxaden | cyprosulfamide | bencarbazone |
| 210 | topramezone | pinoxaden | cyprosulfamide | carfentrazone |
| 211 | topramezone | pinoxaden | cyprosulfamide | carfentrazone-ethyl |
| 212 | topramezone | pinoxaden | cyprosulfamide | cinidon-ethyl |
| 213 | topramezone | pinoxaden | cyprosulfamide | pyraflufen |
| 214 | topramezone | pinoxaden | cyprosulfamide | pyraflufen-ethyl |
| 215 | topramezone | pinoxaden | cyprosulfamide | picolinafen |
| 216 | topramezone | pinoxaden | cyprosulfamide | pyrasulfotole |
| 217 | topramezone | pinoxaden | cyprosulfamide | amino-cyclopyrachlor* |
| 218 | topramezone | pinoxaden | cyprosulfamide | 2,4-D* |
| 219 | topramezone | pinoxaden | cyprosulfamide | 2,4-DB* |
| 220 | topramezone | pinoxaden | cyprosulfamide | 2,4-DP* |
| 221 | topramezone | pinoxaden | cyprosulfamide | 2,4-DP-P* |
| 222 | topramezone | pinoxaden | cyprosulfamide | clopyralid* |
| 223 | topramezone | pinoxaden | cyprosulfamide | dicamba* |
| 224 | topramezone | pinoxaden | cyprosulfamide | fluroxypyr** |
| 225 | topramezone | pinoxaden | cyprosulfamide | MCPA* |
| 226 | topramezone | pinoxaden | cyprosulfamide | MCPB* |
| 227 | topramezone | pinoxaden | cyprosulfamide | MCPP* |
| 228 | topramezone | pinoxaden | cyprosulfamide | MCPP-P* |
| 229 | topramezone | pinoxaden | N-(2-methoxybenzoyl)-4-[(methylaminocarbonyl)amino]benzenesulfonamide | — |
| 230 | topramezone | pinoxaden | N-(2-methoxybenzoyl)-4-[(methylaminocarbonyl)amino]benzenesulfonamide | diclofop |
| 231 | topramezone | pinoxaden | N-(2-methoxybenzoyl)-4-[(methylaminocarbonyl)amino]benzenesulfonamide | diclofop-methyl |
| 232 | topramezone | pinoxaden | N-(2-methoxybenzoyl)-4-[(methylaminocarbonyl)amino]benzenesulfonamide | clodinafop |
| 233 | topramezone | pinoxaden | N-(2-methoxybenzoyl)-4-[(methylaminocarbonyl)amino]benzenesulfonamide | clodinafop-propargyl |
| 234 | topramezone | pinoxaden | N-(2-methoxybenzoyl)-4-[(methylaminocarbonyl)amino]benzenesulfonamide | fenoxaprop |
| 235 | topramezone | pinoxaden | N-(2-methoxybenzoyl)-4-[(methylaminocarbonyl)amino]benzenesulfonamide | fenoxaprop-ethyl |
| 236 | topramezone | pinoxaden | N-(2-methoxybenzoyl)-4-[(methylaminocarbonyl)amino]benzenesulfonamide | fenoxaprop-P |
| 237 | topramezone | pinoxaden | N-(2-methoxybenzoyl)-4-[(methylaminocarbonyl)amino]benzenesulfonamide | fenoxaprop-P-ethyl |
| 238 | topramezone | pinoxaden | N-(2-methoxybenzoyl)-4-[(methylaminocarbonyl)amino]benzenesulfonamide | tralkoxydim |
| 239 | topramezone | pinoxaden | N-(2-methoxybenzoyl)-4-[(methylaminocarbonyl)amino]benzenesulfonamide | amidosulfuron |
| 240 | topramezone | pinoxaden | N-(2-methoxybenzoyl)-4-[(methylaminocarbonyl)amino]benzenesulfonamide | chlorsulfuron |
| 241 | topramezone | pinoxaden | N-(2-methoxybenzoyl)-4-[(methylaminocarbonyl)amino]benzenesulfonamide | florasulam |
| 242 | topramezone | pinoxaden | N-(2-methoxybenzoyl)-4-[(methylaminocarbonyl)amino]benzenesulfonamide | flucarbazone |
| 243 | topramezone | pinoxaden | N-(2-methoxybenzoyl)-4-[(methylaminocarbonyl)amino]benzenesulfonamide | flucetosulfuron |
| 244 | topramezone | pinoxaden | N-(2-methoxybenzoyl)-4-[(methylaminocarbonyl)amino]benzenesulfonamide | flupyrsulfuron |
| 245 | topramezone | pinoxaden | N-(2-methoxybenzoyl)-4-[(methylaminocarbonyl)amino]benzenesulfonamide | imazamox* |
| 246 | topramezone | pinoxaden | N-(2-methoxybenzoyl)-4-[(methylamino- | iodosulfuron |

TABLE A-continued

| # | Compound A | Compound B | Compound C | Compound D |
|---|---|---|---|---|
| 247 | topramezone | pinoxaden | N-(2-methoxybenzoyl)-4-[(methylaminocarbonyl)amino]-benzenesulfonamide | iodosulfuron-methyl-sodium |
| 248 | topramezone | pinoxaden | N-(2-methoxybenzoyl)-4-[(methylaminocarbonyl)amino]-benzenesulfonamide | mesosulfuron-methyl |
| 249 | topramezone | pinoxaden | N-(2-methoxybenzoyl)-4-[(methylaminocarbonyl)amino]-benzenesulfonamide | metazosulfuron |
| 250 | topramezone | pinoxaden | N-(2-methoxybenzoyl)-4-[(methylaminocarbonyl)amino]-benzenesulfonamide | metsulfuron-methyl |
| 251 | topramezone | pinoxaden | N-(2-methoxybenzoyl)-4-[(methylaminocarbonyl)amino]-benzenesulfonamide | propoxycarbazone* |
| 252 | topramezone | pinoxaden | N-(2-methoxybenzoyl)-4-[(methylaminocarbonyl)amino]-benzenesulfonamide | prosulfuron |
| 253 | topramezone | pinoxaden | N-(2-methoxybenzoyl)-4-[(methylaminocarbonyl)amino]-benzenesulfonamide | pyrimisulfan |
| 254 | topramezone | pinoxaden | N-(2-methoxybenzoyl)-4-[(methylaminocarbonyl)amino]-benzenesulfonamide | pyroxsulam |
| 255 | topramezone | pinoxaden | N-(2-methoxybenzoyl)-4-[(methylaminocarbonyl)amino]-benzenesulfonamide | sulfosulfuron |
| 256 | topramezone | pinoxaden | N-(2-methoxybenzoyl)-4-[(methylaminocarbonyl)amino]-benzenesulfonamide | thiencarbazone |
| 257 | topramezone | pinoxaden | N-(2-methoxybenzoyl)-4-[(methylaminocarbonyl)amino]-benzenesulfonamide | thiencarbazone-methyl |
| 258 | topramezone | pinoxaden | N-(2-methoxybenzoyl)-4-[(methylaminocarbonyl)amino]-benzenesulfonamide | thifensulfuron-methyl |
| 259 | topramezone | pinoxaden | N-(2-methoxybenzoyl)-4-[(methylaminocarbonyl)amino]-benzenesulfonamide | triasulfuron |
| 260 | topramezone | pinoxaden | N-(2-methoxybenzoyl)-4-[(methylaminocarbonyl)amino]-benzenesulfonamide | tribenuron-methyl |
| 261 | topramezone | pinoxaden | N-(2-methoxybenzoyl)-4-[(methylaminocarbonyl)amino]-benzenesulfonamide | tritosulfuron |
| 262 | topramezone | pinoxaden | N-(2-methoxybenzoyl)-4-[(methylaminocarbonyl)amino]-benzenesulfonamide | bentazone |
| 263 | topramezone | pinoxaden | N-(2-methoxybenzoyl)-4-[(methylaminocarbonyl)amino]-benzenesulfonamide | bentazone-sodium |
| 264 | topramezone | pinoxaden | N-(2-methoxybenzoyl)-4-[(methylaminocarbonyl)amino]-benzenesulfonamide | bromoxynil |
| 265 | topramezone | pinoxaden | N-(2-methoxybenzoyl)-4-[(methylaminocarbonyl)amino]-benzenesulfonamide | ioxynil |
| 266 | topramezone | pinoxaden | N-(2-methoxybenzoyl)-4-[(methylaminocarbonyl)amino]-benzenesulfonamide | bencarbazone |
| 267 | topramezone | pinoxaden | N-(2-methoxybenzoyl)-4-[(methylaminocarbonyl)amino]-benzenesulfonamide | carfentrazone |
| 268 | topramezone | pinoxaden | N-(2-methoxybenzoyl)-4-[(methylaminocarbonyl)amino]-benzenesulfonamide | carfentrazone-ethyl |
| 269 | topramezone | pinoxaden | N-(2-methoxybenzoyl)-4-[(methylaminocarbonyl)amino]-benzenesulfonamide | cinidon-ethyl |
| 270 | topramezone | pinoxaden | N-(2-methoxybenzoyl)-4-[(methylaminocarbonyl)amino]-benzenesulfonamide | pyraflufen |
| 271 | topramezone | pinoxaden | N-(2-methoxybenzoyl)-4-[(methylaminocarbonyl)amino]-benzenesulfonamide | pyraflufen-ethyl |
| 272 | topramezone | pinoxaden | N-(2-methoxybenzoyl)-4-[(methylaminocarbonyl)amino]-benzenesulfonamide | picolinafen |
| 273 | topramezone | pinoxaden | N-(2-methoxybenzoyl)-4-[(methylaminocarbonyl)amino]-benzenesulfonamide | pyrasulfotole |
| 274 | topramezone | pinoxaden | N-(2-methoxybenzoyl)-4-[(methylaminocarbonyl)amino]-benzenesulfonamide | aminocyclopyrachlor* |
| 275 | topramezone | pinoxaden | N-(2-methoxybenzoyl)-4-[(methylaminocarbonyl)amino]-benzenesulfonamide | 2,4-D* |
| 276 | topramezone | pinoxaden | N-(2-methoxybenzoyl)-4-[(methylaminocarbonyl)amino]-benzenesulfonamide | 2,4-DB* |
| 277 | topramezone | pinoxaden | N-(2-methoxybenzoyl)-4-[(methylaminocarbonyl)amino]-benzenesulfonamide | 2,4-DP* |
| 278 | topramezone | pinoxaden | N-(2-methoxybenzoyl)-4-[(methylaminocarbonyl)amino]-benzenesulfonamide | 2,4-DP-P* |
| 279 | topramezone | pinoxaden | N-(2-methoxybenzoyl)-4-[(methylaminocarbonyl)amino]-benzenesulfonamide | clopyralid* |
| 280 | topramezone | pinoxaden | N-(2-methoxybenzoyl)-4-[(methylaminocarbonyl)amino]-benzenesulfonamide | dicamba* |
| 281 | topramezone | pinoxaden | N-(2-methoxybenzoyl)-4-[(methylaminocarbonyl)amino]-benzenesulfonamide | fluroxypyr** |
| 282 | topramezone | pinoxaden | N-(2-methoxybenzoyl)-4-[(methylaminocarbonyl)amino]-benzenesulfonamide | MCPA* |
| 283 | topramezone | pinoxaden | N-(2-methoxybenzoyl)-4-[(methylaminocarbonyl)amino]-benzenesulfonamide | MCPB* |
| 284 | topramezone | pinoxaden | N-(2-methoxybenzoyl)-4-[(methylaminocarbonyl)amino]-benzenesulfonamide | MCPP* |

TABLE A-continued

| Compound # | Compound A | Compound B | Compound C | Compound D |
|---|---|---|---|---|
| 285 | topramezone | pinoxaden | carbonyl)amino]-benzenesulfonamide N-(2-methoxybenzoyl)-4-[(methylamino-carbonyl)amino]-benzenesulfonamide | MCPP-P* |

*including its salts or esters
**including its esters

The compositions of the present invention are suitable for controlling a large number of harmful plants, including monocotyledonous weeds and dicotyledonous weeds. They are in particular for controlling annual weeds such as gramineous weeds (grasses) including *Echinochloa* species such as barnyardgrass (*Echinochloa crusgalli* var. *crus-galli*), *Digitaria* species such as crabgrass (*Digitaria sanguinalis*), *Setaria* species such as green foxtail (*Setaria vindis*) and giant foxtail (*Setaria faberii*), *Sorghum* species such as johnsongrass (*Sorghum halepense* Pers.), *Avena* species such as wild oats (*Avena fatua*), Cenchrus species such as *Cenchrus echinatus*, *Bromus* species, *Lolium* species, *Phalaris* species, *Eriochloa* species, *Panicum* species, *Brachiaria* species, annual bluegrass (*Poa annua*), blackgrass (*Alopecurus myosuroides*), *Aegilops cylindrica*, *Agropyron repens*, *Apera spica-venti*, *Eleusine indica*, *Cynodon dactylon* and the like. The compositions of the present invention are also suitable for controlling a large number of dicotyledonous weeds, in particular broad leaf weeds including particular broadleaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisllfolia*), *Acanthospermum* species, *Anthemis* species, *Atriplex* species, *Cirsium* species, *Convolvulus* species, *Conyza* species, such as horseweed (*Conyza canadensis*), *Cassia* species, *Commelina* species, *Datura* species, *Euphorbia* species, *Geranium* species, *Galinsoga* species, morningglory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata*, *Bidens pllosa*, *Brassica kaber*, *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus raphanistrum*, *Salsola kali*, *Sinapis arvensis*, *Sonchus arvensis*, *Thlaspi arvense*, *Tagetes minuta*, *Richardia braslliensis*, and the like.

The compositions of the present invention are suitable for combating/controlling undesired vegetation in small-grain cereal crops, such as wheat, durum, triticale, rye and barley.

If not stated otherwise, the compositions of the invention are suitable for application in any variety of the aforementioned crop plants.

The compositions according to the invention can also be used in crop plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetylCoA carboxylase (ACCase) inhibitors; or oxynil (i.e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutgenesis and conventional methods of breeding, e.g., Clearfield® summer rape (Canola, BASF SE, Germany) being tolerant to imidazolinones, e.g., imazamox, or Express-Sun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

The compositions according to the invention can also be used in genetically modified crop plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

The compositions according to the invention can also be used in crop plants that have been modified, e.g. by the use of recombinant DNA techniques to be capable of synthesizing one or more insecticidal proteins, especially those known from the bacterial genus *Bacillus*, particularly from *Bacillus thuringiensis*, such as delta-endotoxins, e.g., CryIA(b), CryIA(c), CryIF, CryIF(a2), CryIIA(b), CryIIIA, CryIIIB (b1) or Cry9c; vegetative insecticidal proteins (VIP), e.g., VIP1, VIP2, VIP3 or VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, or other insect-specific neurotoxins; toxins produced by fungi, such as *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e.g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

The compositions according to the invention can also be used in crop plants that have been modified, e.g. by the use of recombinant DNA techniques to be capable of synthesizing one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato cultivars, which express resistance genes acting against *Phytophthora infestans* derived from the Mexican wild potato, *Solanum bulbocastanum*) or T4-lysozym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

The compositions according to the invention can also be used in crop plants that have been modified, e.g. by the use of recombinant DNA techniques to be capable of synthesizing one or more proteins to increase the productivity (e.g., biomass production, grain yield, starch content, oil content or protein content), tolerance to drought, salinity or other growth-limiting environmental factors or tolerance to pests and fungal, bacterial or viral pathogens of those plants.

The compositions according to the invention can also be used in crop plants that have been modified, e.g. by the use of recombinant DNA techniques to be capable of producing an increased amount of ingredients or new ingredients, which are suitable to improve human or animal nutrition, e.g., oil crops that produce health-promoting long-chain omega-3 fatty acids or unsaturated omega-9 fatty acids (e.g., Nexera® rape, Dow AgroSciences, Canada).

The compositions of the present invention can be applied in a conventional manner by a skilled personal familiar with the techniques of applying herbicides. Suitable techniques include spraying, atomizing, dusting, spreading or watering. The type of application depends on the intended purpose in a well known manner; in any case, they should ensure the finest possible distribution of the active ingredients according to the invention.

The compositions can be applied pre- or post-emergence, i.e. before, during and/or after emergence of the undesirable plants. When the compositions are used in crops, they can be applied after seeding and before or after the emergence of the crop plants. The compositions invention can, however, also be applied prior to seeding of the crop plants.

It is a particular benefit of the compositions according to the invention that they have a very good post-emergence herbicide activity, i.e. they show a good herbicidal activity against emerged undesirable plants. Thus, in a preferred embodiment of invention, the compositions are applied post-emergence, i.e. during and/or after, the emergence of the undesirable plants. It is particularly advantageous to apply the mixtures according to the invention post emergent when the undesirable plant starts with leaf development up to flowering. Since the compositions of the present invention show good crop tolerance, even when the crop has already emerged, they can be applied after seeding of the crop plants and in particular during or after the emergence of the crop plants.

In any case herbicide compound A, and the compound B and, if desired, herbicide component C and/or safener D, can be applied simultaneously or in succession.

The compositions are applied to the plants mainly by spraying, in particular foliar spraying. Application can be carried out by customary spraying techniques using, for example, water as carrier and spray liquor rates of 10 to 2000 l/ha or 50 to 1000 l/ha (for example from 100 to 500 l/ha). Application of the herbicidal compositions by the low-volume and the ultra-low-volume method is possible, as is their application in the form of microgranules.

In the case of a post-emergence treatment of the plants, the herbicidal mixtures or compositions according to the invention are preferably applied by foliar application. Application may be effected, for example, by usual spraying techniques with water as the carrier, using amounts of spray mixture of approx. 50 to 1000 l/ha.

In the method of the invention, the application rate of the herbicide compound A, calculated as topramezone, is from generally from 5 to 50 g/ha and in particular from 8 to 25 g/ha.

In the method of the invention, the application rate of pinoxaden is generally from 25 to 75 g/ha and in particular from 40 to 60 g/ha.

In the method of the invention, the application rate of the herbicide safener compound C (in case of salts calculated as the acid) is generally from 5 to 75 g/ha and in particular from 10 to 50 g/ha.

In the method of the invention, the application rate of the further herbicide compound D (in case of salts calculated as the acid) is generally from 1 to 2500 g/ha and in particular from 5 to 1000 g/ha.

The rate of application of the synthetic lipid biosynthesis inhibitors, in particular ACCase inhibitors, mentioned as group D.1 is generally from 5 to 750 g/ha, in particular from 10 to 500 g/ha of active substance (a.s.).

The rate of application of the ALS inhibitors mentioned as group D.2 is generally from 1 to 500 g/ha, in particular from 3 to 200 g/ha of active substance (a.s.).

The rate of application of the PSII inhibitors mentioned as group D.3 is generally from 5 to 1000 g/ha, in particular from 10 to 500 g/ha of active substance (a.s.).

The rate of application of the protox inhibitors mentioned as group D.4 is generally from 1 to 1000 g/ha, in particular from 5 to 500 g/ha of active substance (a.s.).

The rate of application of the bleacher herbicides mentioned as group D.5 is generally from 5 to 750 g/ha, in particular from 10 to 500 g/ha of active substance (a.s.).

The rate of application of the auxinic herbicides mentioned as group D.6 is generally from 5 to 2500 g/ha, in particular from 10 to 1500 g/ha of active substance (a.s.).

The present invention also relates to formulations of the compositions according to the present invention. The formulations contain, besides the composition, at least one organic or inorganic carrier material. The formulations may also contain, if desired, one or more surfactants and, if desired, one or more further auxiliaries customary for crop protection compositions.

The formulation may be in the form of a single package formulation containing both the herbicide compound A and pinoxaden, and, if desired, herbicide safener compound C and/or further herbicide D, together with liquid and/or solid carrier materials, and, if desired, one or more surfactants and, if desired, one or more further auxiliaries customary for crop protection compositions. The formulation may be in the form of a two package formulation, wherein one package contains a formulation of herbicide compound A while the other package contains a formulation of the pinoxaden and, if desired, herbicide safener compound C and/or further herbicide compound D, and wherein both formutations contain at least one carrier material, if desired, one or more surfactants and, if desired, one or more further auxiliaries customary for crop protection compositions. The formulation may also be in the form of a two package formulation, wherein one package contains a formulation of herbicide compound A and pinoxaden and optionally the herbicide safener compound C, while the other package contains a formulation of the further herbicide compound D, and wherein both formulations contain at least one carrier material, if desired, one or more surfactants and, if desired, one or more further auxiliaries customary for crop protection compositions. In the case of two package formulations the two formulations are preferably mixed prior to application. Preferably the mixing is performed as a tank mix, i.e. the formulations are mixed immediately prior or upon dilution with water.

In the formulation of the present invention the active ingredients, i.e. herbicide compound A, pinoxaden and optional further actives (e.g. herbicide safener C and/or further herbicide compound D) are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

Depending on the formulation type, they comprise one or more liquid or solid carriers, if appropriate surfactants (such as dispersants, protective colloids, emulsifiers, wetting agents and tackifiers), and if appropriate further auxiliaries which are customary for formulating crop protection products. The person skilled in the art is sufficiently familiar with the recipes for such formulations. Further auxiliaries include e.g. organic and inorganic thickeners, bactericides, antifreeze agents, antifoams, colorants and, for seed formulations, adhesives.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T.

Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

To prepare emulsions, pastes or oil dispersions, the active the components, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Powders, materials for spreading and dusts can be prepared by mixing or concomitant grinding of the active the components A and B and optionally safener C and optionally herbicide D with a solid carrier.

Granules, e.g. coated granules, impregnated granules and homogeneous granules, can be prepared by binding the active ingredients to solid carriers.

The formulations of the invention comprise a herbicidally effective amount of the composition of the present invention. The concentrations of the active ingredients in the formulations can be varied within wide ranges. In general, the formulations comprise from 1 to 98% by weight, preferably 10 to 60% by weight, of active ingredients (sum of topramezone, herbicide compound B and optionally further active compounds). The active ingredients are employed in a purity of from 90% to 100%, preferably 95% to 100% (according to NMR spectrum).

The active herbicide compounds A and B as well as the compositions according to the invention can, for example, be formulated as follows:

1. Products for Dilution with Water

A Water-Soluble Concentrates 10 parts by weight of active compound (or composition) are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound (or composition) are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound (or composition) are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound (or composition) are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound (or composition) are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound (or composition) are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound (or composition) are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound (or composition), 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound (or composition) are ground finely and mixed intimately with 95 parts by weight of finely divided kaolin. This gives a dusting powder with an active compound content of 5% by weight.

J Granules (GR, FG, GG, MG)

0.5 parts by weight of active compound (or composition) are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound (or composition) are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

It may furthermore be beneficial to apply the compositions of the invention alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

Use Examples

The effect of the herbicidal compositions according to the invention of herbicides compound A and pinoxaden and, if appropriate, herbicide safener compound C and/or further herbicide compound D on the growth of undesirable plants compared to the herbicidally active compounds alone was demonstrated by the following greenhouse experiments:

The culture containers used were plastic pots containing loamy sand with approximately 3.0% of humus as substrate. The seeds of the test plants were sown separately for each species.

For the pre-emergence and post-emergence treatments, topramezone, pinoxaden and the herbicide safener compounds C and herbicide compounds D, which had been suspended or emulsified in water, were applied by means of finely/evenly distributing spray nozzles. In all use examples, plants were grown in a greenhouse environment.

For the pre-emergence treatment, the active compounds, suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active compounds.

For the post-emergence treatment, the test plants were grown to growth stage 10 to 22, depending on the plant variety or to a height, depending on the plant habit, and only then treated with the active compounds which had been suspended or emulsified in water. To this end, the test plants were either sown directly and grown in the same containers, or they were first grown separately as seedlings and transplanted into the test containers a few days prior to treatment.

Depending on the species, the plants were kept at 10-25° C. and 20-35° C., respectively. The test period extended over 1 to 4 weeks. During this time, the plants were tended and their response to the individual treatments was evaluated.

The herbicide compounds applied in the examples were used as commercially available formulations which have been diluted with tap water to a suitable concentration. Topramezone was used as a commercial suspension concentrate (Clio® of BASF SE) having an active ingredient concentration of 336 g/l. Pinoxaden (herbicide B) and cloquintocet-mexyl (safer compound C) were used as a commercial aqueous emulsion concentrate (Axial® of Syngenta) having an active ingredient concentration of 100 g/l of pinoxaden and 25 g/l of cloquintocet-mexyl.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
| --- | --- | --- |
| Galium aparine | GALAP | cleaver |
| Hordeum vulgare | HORVW | winter barley |
| Triticum aestivum | TRZAW | winter wheat |
| Veronica persica | VERPE | field speedwell |

Colby's formula was applied to determine whether the composition showed synergistic action: S. R. Colby (1967) "Calculating synergistic and antagonistic responses of herbicide combinations", Weeds 15, p. 22 ff.

$$E = X + Y - (X \cdot Y/100)$$

where

X = effect in percent using herbicide A at an application rate a;

Y = effect in percent using pinoxaden (herbicide B) at application rate b or a combination of pinoxaden and safener C at application rates b and c;

E = expected effect (in %) of A+B at application rates a+b or of A+B+C at application rates a+b+c.

For mixtures of three herbicide compounds a modified Colby formula can be used:

$$E = X + Y + Z - [(X \cdot Y + X \cdot Z + Y \cdot Z)/100] - X \cdot Y \cdot Z/10000$$

where E, X and Y are as defined above and Z is the herbicide effect in percent using herbicide compound D (or a combination of herbicide compounds D) at an application rate d.

The value E corresponds to the effect (plant damage or injury) which is to be expected if the activity of the individual compounds is just additive. If the observed effect is higher than the value E calculated according to Colby, a synergistic effect is present.

Table 1 shows the wheat and barley herbicide damage ratings in post-emergence application assessed 27 DAT. Table 2 shows the herbicidal activity against *Galium aparine* and *Veronica persica* in post-emergence application assessed 27 DAT. The data show that the mixtures according to the invention are highly selective in wheat and barley and show synergistic weed control against cleavers and field speedwell.

TABLE 1

Post-emergence herbicidal activity of topramezone and pinoxaden/-cloquintocet-mexyl against wheat and barley (27 DAT)

| Use rate (g a. i/ha) | | | Herbicidal activity (%) at 27 DAT | | |
| --- | --- | --- | --- | --- | --- |
| | | | TRZAW | TRZAS | HORVW |
| Topramezone | Pinoxaden | Cloquintocet-mexyl | Cubus GS12 | Taifun GS11 | Highlight GS11 |
| 12 | 0 | 0 | 20 | 30 | 20 |
| 0 | 24 | 6 | 0 | 0 | 0 |
| 12 | 24 | 6 | 0 | 0 | 5 |
| 0 | 12 | 3 | 0 | 0 | 0 |
| 12 | 12 | 3 | 0 | 0 | 0 |

TABLE 2

Post-emergence herbicidal activity of topramezone and pinoxaden/-cloquintocet-mexyl against GALAP and VERPE (27 DAT)

| Use rate (g a.i./ha) | | | Herbicidal activity (%) at 27 DAT | | | |
|---|---|---|---|---|---|---|
| | | | Observed | | Expected according to Colby's formula | |
| Topra-mezone | Pinoxaden | Cloquin-tocet-mexyl | GALAP GS22 | VERPE GS22 | GALAP GS22 | VERPE GS22 |
| 12 | 0 | 0 | 90 | 75 | n.a. | n.a. |
| 0 | 24 | 6 | 10 | 0 | n.a. | n.a. |
| 12 | 24 | 6 | 95 | 100 | 91 | 75 |
| 0 | 12 | 3 | 0 | 0 | n.a. | n.a. |
| 12 | 12 | 3 | 95 | 100 | 90 | 75 |

We claim:

1. A herbicidal composition comprising:
   a) a herbicide compound A which is selected from topramezone, the salts and esters, carbonates or thiocarbonates thereof;
   and
   b) a second herbicide compound B which is pinoxaden; and
   c) a herbicide safener compound C, which is selected from cloquintocet, a salt or an ester thereof; wherein the weight ratio of the herbicide compound A and the herbicide compound B is from 1:1 to 1:15 and the weight ratio of the herbicide compound A and the herbicide safener compound C is from 4:1 to 1:7, wherein the herbicide compound A is calculated as topramezone.

2. The composition as claimed in claim 1, wherein the weight ratio of the herbicide compound A and the herbicide safener compound C is from 4:1 to 1:1, wherein the herbicide compound A is calculated as topramezone.

3. The composition as claimed in claim 1, wherein the composition further comprises at least one herbicide compound D which is selected from the group consisting of
   D.1 synthetic lipid biosynthesis inhibitors;
   D.2 acetolactate synthase inhibitors;
   D.3 photosynthesis inhibitors;
   D.4 protoporphyrinogen-IX-oxidase inhibitors;
   D.5 bleacher herbicides; and
   D.6 auxinic herbicides.

4. The composition as claimed in claim 3, wherein the at least one herbicide compound D is a synthetic lipid biosynthesis inhibitor selected from the group consisting of clodinafop, diclofop, fenoxaprop, fenoxaprop-P and tralkoxydim and, where applicable, a salt or an ester thereof.

5. The composition as claimed in claim 3, wherein the at least one herbicide compound D is an acetolactate synthase inhibitor selected from the group consisting of amidosulfuron, chlorsulfuron, florasulam, flucarbazone, flucetosulfuron, flupyrsulfuron, imazamox, iodosulfuron, mesosulfuron-methyl, metazosulfuron, metsulfuron-methyl, propoxycarbazone, prosulfuron, pyrimisulfan, pyroxsulam, sulfosulfuron, thiencarbazone, thifensulfuron-methyl, triasulfuron, tribenuron-methyl, tritosulfuron and, where applicable, a salt or an ester thereof.

6. The composition as claimed in claim 3, wherein the at least one herbicide compound D is an inhibitor of photosynthesis which selected from the group consisting of bentazone, bromoxynil, ioxynil and, where applicable, a salt or an ester thereof.

7. The composition as claimed in claim 3, wherein the at least one herbicide compound D is a protoporphyrinogen-IX-oxidase inhibitor selected from the group consisting of bencarbazone, carfentrazone, cinidon-ethyl, pyraflufen and, where applicable, a salt or an ester thereof.

8. The composition as claimed in claim 3, wherein the at least one herbicide compound D is a bleacher herbicide selected from the group consisting of picolinafen and pyrasulfotole.

9. The composition as claimed in claim 3, wherein the at least one herbicide compound D is an auxinic herbicide selected from the group consisting of aminocyclopyrachlor, 2,4-D, 2,4-DB, 2,4-DP, 2,4-DP-P, clopyralid, dicamba, fluroxypyr, MCPA, MCPB, MCPP, MCPP-P and, where applicable, a salt or an ester thereof.

10. The composition as claimed in claim 3, wherein the weight ratio of the herbicide compound A and the total amount of the herbicide compound B and the at least one herbicide compound D is from is from 1:1 to 1:500, wherein the herbicide compound A is calculated as topramezone and wherein each herbicide compound D, which is an ester or a salt of an acid, is calculated as the acid.

11. The composition as claimed in claim 3, wherein the weight ratio of the second herbicide compound B and the at least one herbicide compound D is from 10:1 to 1:100, wherein each herbicide compound D, which is an ester or a salt of an acid, is calculated as the acid.

12. An herbicide formulation comprising a composition as claimed in claim 1 and at least one solid or liquid carrier.

13. A method for controlling undesirable vegetation in cereal crop, which comprises applying a composition as claimed in claim 1 on plants to be controlled or their habitat.

14. The method as claimed in claim 13, where the composition is applied in cultures of crop plants.

15. The method as claimed in claim 14, where the crop plants are cereal crop plants.

16. The method as claimed in claim 14, which comprises applying the composition as claimed in claim 1 during and/or after the emergence of the plants to be controlled, the herbicide compounds A and B and optionally the at least one herbicide safener compound C and/or the further herbicide compound D being applied simultaneously or in succession.

17. The method as claimed in claim 13, where the herbicide compound A is applied in an amount from 5 to 50 g/ha.

18. The method as claimed in claim 13, where the herbicide compound B is applied in an amount from 25 to 75 g/ha.

19. The method as claimed in claim 13, where the herbicide safener compound C is applied in an amount from 5 to 75 g/ha.

20. The method as claimed in claim 13, where the herbicide compound D is applied in an amount from 1 to 2500 g/ha.

* * * * *